(12) United States Patent
Van Der Heide et al.

(10) Patent No.: US 8,901,325 B2
(45) Date of Patent: Dec. 2, 2014

(54) METHOD FOR PRODUCING FURFURAL FROM LIGNOCELLULOSIC BIOMASS MATERIAL

(75) Inventors: Evert Van Der Heide, Amstedam (NL); Ting Zhang, Amsterdam (NL)

(73) Assignee: Shell Oil Company, Houston, TX (US)

(*) Notice: Subject to any disclaimer, the term of this patent is extended or adjusted under 35 U.S.C. 154(b) by 666 days.

(21) Appl. No.: 12/970,131

(22) Filed: Dec. 16, 2010

(65) Prior Publication Data
US 2011/0144359 A1 Jun. 16, 2011

(30) Foreign Application Priority Data
Dec. 16, 2009 (EP) .................................... 09179462

(51) Int. Cl.
*C07D 307/50* (2006.01)
*C07D 307/48* (2006.01)

(52) U.S. Cl.
CPC ............ *C07D 307/48* (2013.01); *C07D 307/50* (2013.01)
USPC ........................................................ 549/489

(58) Field of Classification Search
CPC .................................................... C07D 307/50
USPC ........................................................ 549/489
See application file for complete search history.

(56) References Cited

U.S. PATENT DOCUMENTS

| | | | |
|---|---|---|---|
| 1,946,688 A * | 2/1934 | Groth et al. | 549/489 |
| 4,916,242 A | 4/1990 | Avignon et al. | 549/489 |
| 2006/0229458 A1 | 10/2006 | Ahmed | 549/429 |
| 2007/0259412 A1 | 11/2007 | Belanger et al. | 435/161 |
| 2008/0299628 A1 | 12/2008 | Hallberg et al. | 435/139 |

FOREIGN PATENT DOCUMENTS

| | | | |
|---|---|---|---|
| CA | 1339664 | 2/1998 | C07C 59/185 |
| EP | 0346836 | 12/1989 | C07D 307/50 |
| FR | 2556344 | 6/1985 | C07D 307/50 |
| WO | WO7900119 | 3/1979 | D21C 3/20 |
| WO | WO9726403 | 7/1997 | D21C 3/04 |
| WO | WO0068494 | 11/2000 | D21C 3/20 |
| WO | WO2006086861 | 8/2006 | C13K 1/02 |
| WO | WO2007051269 | 5/2007 | C13K 1/02 |
| WO | WO2007120210 | 10/2007 | C12P 7/10 |
| WO | WO2009080737 | 7/2009 | C12P 7/10 |

OTHER PUBLICATIONS

Uppal et al, Suger Tech, vol. 10 (4), p. 298-301 (2008).*
Ballesteros et al, Applied Biochemistry and Biotechnology, vol. 136-140, p. 239-252 (2007).*
Allen et al, Industrialand Engineering Chemistry Research, vol. 40, p. 2934-2941 (2001).*
Zhuang ei al (I), BioResources, vol. 4(3), p. 1147-1157 (2009).*
Zhuang et al (II), Bio Resources, vol. 4(2), p. 674-686 (2009).*

(Continued)

*Primary Examiner* — Andrew D Kosar
*Assistant Examiner* — Raymond Covington

(57) ABSTRACT

A method for producing furfural from lignocellulosic biomass material is provided, comprising (a) contacting the lignocellulosic biomass material with a mixture comprising water and an organic acid at a temperature of at least 100° C. and a pressure of at most 10 bar (absolute) to obtain a first liquid stream comprising hydrolyzed hemicellulose and a second stream comprising lignin and cellulose; (b) maintaining the first liquid stream comprising hydrolyzed hemicellulose at a temperature of at least 130° C. to obtain a second liquid stream comprising furfural; and (c) separating the furfural obtained in step b) from the second liquid stream.

12 Claims, 1 Drawing Sheet

(56) References Cited

OTHER PUBLICATIONS

Singh et al, Ind. Eng. Chem. Prod. Res. Dev., vol. 23, p. 257-262 (1984).*

D.R. Lide et al., CRC Handbook of Chemistry & Physics, CRC Press Inc, Boston, 77$^{th}$ Ed., 1996, pp. 6-13 to 6-14.

Xuejun Pan et al., "Biorefining of Softwoods Using Ethanol Organosolv Pulping: Preliminary Evaluation of Process Streams for Manufacture of Fuel-Grade Ethanol and Co-Products", Published online Mar. 16, 2005, Wiley InterScience (www.interscience.wiley.com), pp. 473-481.

S. Dapia et al., "Study of Formic Acid as an Agent for Biomass Fractionation," Biomass and Bioenergy 22 (2002), pp. 213-221, XP-002584824.

N. Abatzoglou et al., "Dilute Acid Hydrolysis of Lignocellulosics. An Application to Medium Consistency Suspensions of Hardwoods Using a Plug Flow Reactor", Canadian Journal of Chemical Engineering, 1990 68(8), pp. 627-638.

Ann H. Brennan et al. "High Temperature Acid Hydrolysis of Biomass Using an Engineering-Scale Plug Flow Reactor: Results of Low Solids Testing," Biotechnology and Bioengineering Symposium No. 17 (1986) pp. 53-70.

PCT, International Search Report, Application No. PCT/EP2010/069750 dated Apr. 14, 2011.

Claudio Arato et al., "The Lignol Approach to Biorefining of Woody Biomass to Produce Ethanol and Chemicals," Applied Biochemistry and Biotechnology, vol. 121-124, 2005, pp. 871-882.

Karl J. Zeitsch, "The Chemistry and Technology of Furfural and its Many By-Products", Elsevier, 2000.

PCT, International Search Report, Application No. PCT/EP2010/069750 dated Jan. 18, 2011.

* cited by examiner

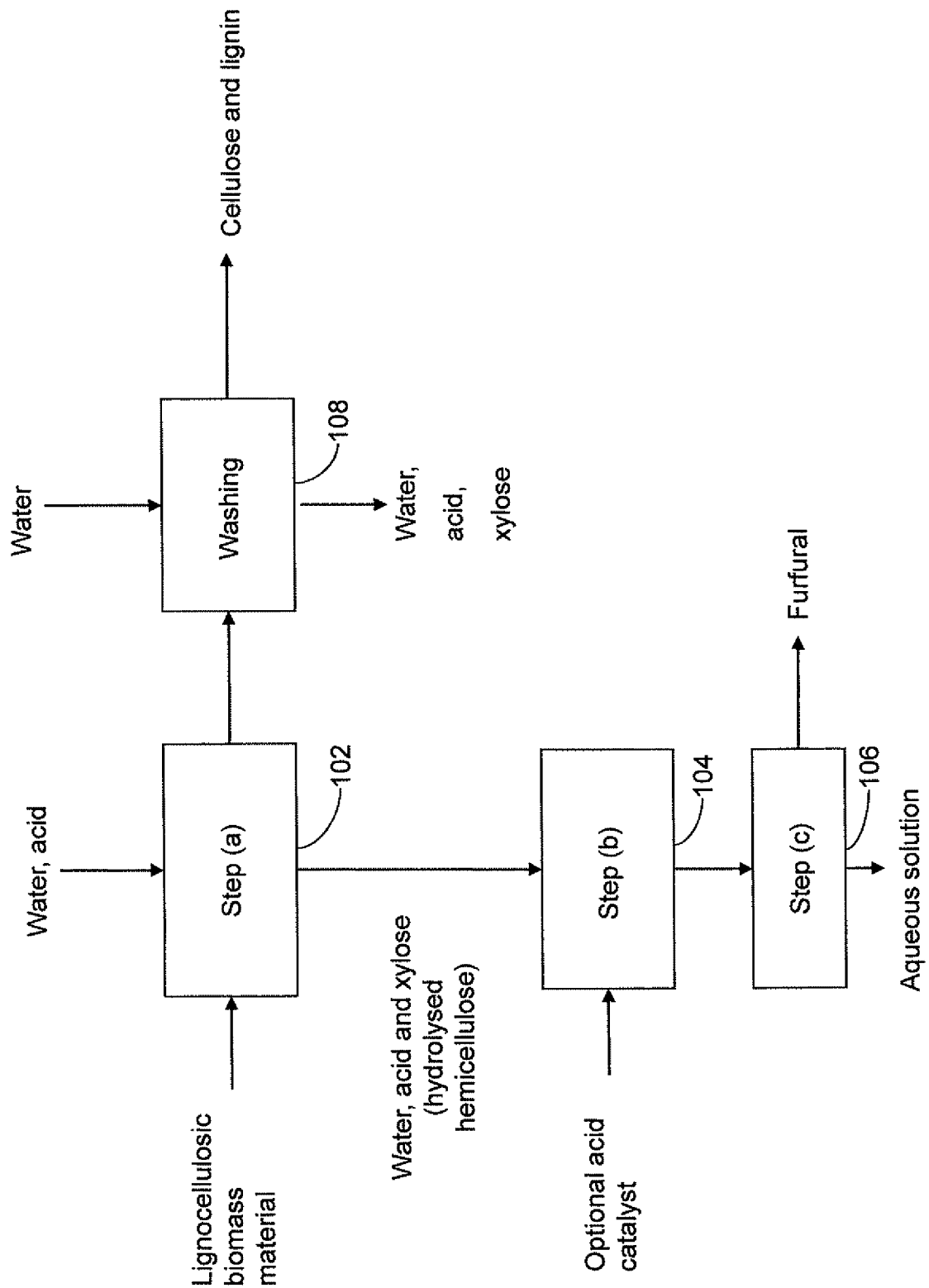

METHOD FOR PRODUCING FURFURAL FROM LIGNOCELLULOSIC BIOMASS MATERIAL

This application claims the benefit of European Application No. 09179462.8 filed Dec. 16, 2009 which is incorporated herein by reference.

FIELD OF THE INVENTION

The present invention relates to a method for producing furfural from lignocellulosic biomass material.

BACKGROUND OF THE INVENTION

With the diminishing supply of crude oil, the use of renewable energy sources is becoming increasingly important as a feedstock for production of hydrocarbon compounds. Plants and animal biomass are being used to produce liquid and gaseous hydrocarbon compounds. One of the advantages of using biomass is that the $CO_2$ balance is more favourable as compared with the conventional hydrocarbon feedstock.

One of the most commonly used biomass material used is lignocellulosic biomass material. Lignocellulosic biomass materials primarily consist of cellulose, hemicellulose, and lignin bonded together in a complex gel structure along with optional small quantities of extractives, pectins, proteins, and/or ash.

Cellulose and hemicellulose, when hydrolysed into sugars, can be further converted into ethanol and other useful products and intermediates, for example through microbiological fermentation technologies or through thermochemical conversions, such as aqueous phase reforming. In addition hemicellulose present in the lignocellulosic biomass material can be processed to obtain sugars which can later be converted to fuels and chemicals, such as furfurals. Furfural has various applications in the chemical and petrochemical industry and the derivatives of furfural are also useful as polymers and resins.

Various problems associated with the production of the furfural arise due to the complex chemical structure of the lignocellulosic biomass material. The separation of the hemicellulose from other lignocellulosic constituents is complicated by the fact that lignin can be intertwined and linked in various ways with cellulose and hemicellulose. Pretreatment of the lignocellulosic biomass material makes the individual components more accessible for processing, thereby easing the production of furfural from hemicellulose. Existing pretreatment processes, however, have several drawbacks.

The use of organic solvents, such as formic acid and acetic acid, in pretreatment procedures has the disadvantage that solvent recovery is a cumbersome and expensive process step.

The use of steam for destructuring/decomposition of biomass, such as for example by "Steam explosion", "steam cooking", "pressure cooking in water", "dilute acid hydrolysis", "liquid hot water pretreatment", and "hydrothermal treatment", has the disadvantage that they are carried out at higher pressures and may change the properties of lignocellulosic biomass materials. This can result in degradation of sugars and formation of inhibitors.

EP-346836 describes a process and apparatus for continuous preparation of 2-furaldehyde, cellulose and lignin from lignocellulosic material. The described process requires a lignocellulosic material with a reduced particle size in the range from about 2 to about 10 mm. This lignocellulosic material is first swelled at 70 to 90° C., whereafter part of the water is extorted. The remaining suspension of lignocellulosic material in water is hydrolysed in a first hydrolyse step at 115 to 135° C., whereafter again part of the liquid is extorted. Hereafter the remaining suspension of lignocellulosic material in water is hydrolysed in a second hydrolyse step in two stages from 160° C. to 180° C. and 200° C. to 235° C. respectively, whereafter again part of the liquid is extorted. This last liquid also contains 2-furaldehyde. A disadvantage of the process as described in EP-346836 are the many steps and the large amount of volumes, energy and equipment needed.

In organosolv pretreatment processes a lignin-extracting solvent blend is used to extract lignin in high temperature and high pressure digesters. Examples of such organosolv pretreatment processes can be found in WO200686861, WO200751269 US20070259412 and US 2008/0299628. However, the organosolv pretreatments have high capital costs, high energy requirement, problems with solvent recovery and less efficiency.

Accordingly, these pretreatment processes share one or several of the shortcomings which include severe pretreatment conditions, high capital costs, high energy requirement and problems of solvent recovery and less efficiency of the pretreatment.

SUMMARY OF THE INVENTION

An effective and simple method for the pretreatment of lignocellulosic biomass material and subsequent production of furfural has now been found.

Accordingly, in one embodiment of the present invention, a method for producing furfural from lignocellulosic biomass material is provided, comprising the steps of: (a) contacting the lignocellulosic biomass material with a mixture comprising water and an organic acid at a temperature of at least 100° C. and a pressure not greater than 10 bar (absolute) to obtain a first liquid stream comprising hydrolysed hemicellulose and a second stream comprising lignin and cellulose; (b) maintaining the first liquid stream comprising hydrolysed hemicellulose at a temperature of at least 130° C. to obtain a second liquid stream comprising furfural; and (c) separating the furfural obtained in step b) from the second liquid stream.

Such method allows for lignocellulosic biomass material to be efficiently used for the production of furfural after it has been pre-treated. Advantageously the method makes it possible to carry out the complete process whilst using the same catalyst(s) in all steps. Furthermore such method avoids the need to reheat any liquid stream in step b) and makes efficient use of the heat applied in step a).

In addition, the method allows the use of high solids content and even allows the use of weight ratios of solid to solvent in the range of 1:3 to 1:5.

Further in one embodiment of the invention method advantageously allows the process to be carried out in one reactor.

BRIEF DESCRIPTION OF THE DRAWING

FIG. 1 shows a schematic diagram of the method according to the invention.

DETAILED DESCRIPTION

In step (a), the lignocellulosic biomass material is contacted with a mixture containing water and an organic acid at a temperature of at least 100° C. and a pressure not greater than 10 bar (absolute) to obtain a first liquid stream containing hydrolysed hemicellulose and a second stream containing lignin and cellulose and any remnants of hemicellulose.

By a lignocellulosic biomass material is herein understood a material containing lignocellulose obtained directly or indirectly from a biological source. Preferably it is understood to be a naturally obtained lignocellulosic material.

Examples of lignocellulosic biomass material include any lignocellulose containing biological materials, such as agriculture waste, forest residue, wood chips, straw, chaff, grain, grasses, corn, corn husks, weeds, aquatic plants and/or hay; and/or any lignocellulose containing material of biological origin, such as some municipal waste or household waste.

Any lignocellulosic biomass material known to be suitable for hydrolysis by the person skilled in the art may be used in the method according to the present invention. The method of the invention is in particularly suited for conversion of non-wood lignocellulosic biomass material, particularly grass-derived lignocellulosic biomass material. Typical grasses include wheat straw, but also miscanthus, sweet sorghum and bamboo.

The lignocellulosic biomass material typically includes hemicellulose, lignin and cellulose. In one embodiment, the hemicellulose present in the lignocellulosic biomass material is processed to produce furfural.

The hemicellulose preferably contains one or more amorphous polymers of five and six carbon sugars. The lignocellulosic biomass material may for example include hemicelluloses in an amount of from 10 wt. % to 50 wt. %, more preferably in an amount of from 20 wt. % to 30 wt. %.

The lignin preferably comprises a highly cross-linked polymer of phenolic compounds. The lignocellulosic biomass material may for example include lignin in an amount of from 1 wt. % to 40 wt. %, more preferably in an amount of from 5 wt. % to 30 wt. %.

The cellulose preferably comprises a highly crystalline polymer of cellobiose, a glucose dimer. The lignocellulosic biomass material in the method according to the invention may for example include cellulose in an amount of from 10 wt. % to 50 wt. %, more preferably in an amount of from 30 wt. % to 40 wt. %.

Without wishing to be bound by any kind of theory it is believed that the cellulose, hemicellulose, and lignin are bonded together in a complex gel structure along with optional small quantities of extractives, pectins, proteins, and/or ash.

Cellulose and hemicellulose, when hydrolysed into their sugars, can be converted into ethanol or other useful compounds through any kind of fermentation technology known by the skilled person to be suitable for this purpose. These sugars may also advantageously form the feedstock for production of a variety of chemicals and polymers, through microbial fermentation or through thermochemical processes, such as aqueous phase reforming.

In a preferred embodiment the lignocellulosic biomass material is rich in pentosans. By a pentosan is understood a type of hemicellulose comprising a polymer of pentose sugars. By a pentose sugar is understood a monosaccharide with five carbon atoms. Examples of preferred pentose sugars include xylose and arabinose. Such pentose sugars can advantageously be converted into furfural.

Preferably the lignocellulosic biomass material in the method of the invention comprises equal to or more than 1 wt % of pentosans, more preferably equal to or more than 3 wt % pentosan, still more preferably equal to or more than 5 wt % pentosans most preferably equal to or more than 10 wt % pentosans. Although there is no upper limit, for practical purposes, the lignocellulosic biomass material used as a feed in the process of the invention may comprise equal to or less than 90 wt % pentosans, preferably equal to or less than 60 wt % pentosans, more preferably equal to or less than 40 wt % pentosans and most preferably equal to or less than 35 wt % pentosans.

In a preferred embodiment the lignocellulosic biomass comprises particles with an weight average length (that is the longest diameter of the particle) preferably in the range from equal to or more than 0.5 millimeter, more preferably equal to or more than 1 millimeter to equal to or less than 5 centimeter, more preferably to equal to or less than 2.5 centimeters and preferably an average constituent thickness or weight average thickness (that is the shortest diameter of the particle) in the range from equal to or more than 0.01 millimeter, more preferably equal to or more than 0.1 millimeter, to equal to or less than 2.5 centimeter, more preferably to equal to or less than 1 centimeters, most preferably equal to or less than 0.2 centimeters.

If necessary, the particle size of the lignocellulosic biomass material can be reduced before its use in contacting step a). Such a reduction of particle size can be achieved in any manner known to the skilled person to be suitable for this purpose. Suitable methods for particle size reduction include crushing, grinding, milling, cutting, chipping, shredding, granulation and/or any combination thereof.

The lignocellulosic biomass material is subjected to an elevated temperature and pressure in the presence of water and an organic acid to hydrolyse hemicellulose. That is, the lignocellulosic biomass material is contacted with the mixture comprising water and organic acid at a temperature of at least 100° C. and a pressure not greater than 10 bar to hydrolyse at least part of the hemicellulose comprised in the lignocellulosic biomass material such that hydrolysed hemicellulose is obtained.

The lignocellulosic biomass material-to-mixture weight ratio (i.e. the weight ratio of solid to solvent) is preferably in the range of from 2-to-1 (2:1) to 1-to-10 (1:10), more preferably in the range of from 1-to-3 (1:3) to 1-to-8 (1:8), most preferably in the range from 1-to-3 (1:3) to 1-to-5 (1:5).

The organic acid in the mixture comprising water and organic acid is preferably formic acid, acetic acid, citric acid and/or oxalic acid. Without wishing to be bound by any kind of theory, it is believed that the organic acid may serve the purpose of a catalyst thereby aiding in the hydrolysis of the hemicellulose and also helping in destructuring (decomposing) of the lignin.

In step a) the weight percentage of the organic acid in the mixture comprising water and organic acid is preferably in the range of from 0.1 to 20 wt %, more preferably in the range of from 0.1 to 10 wt %, most preferably in the range of from 0.1 to 5 wt %.

The mixture comprising water and an organic acid may preferably comprise in addition an inorganic acid, preferably hydrochloric acid, sulphuric acid, nitric acid and/or phosphoric acid.

Step a) of the method of the invention is preferably performed at a temperature range of from 100 to 220° C., more preferably in the range of from 130 to 180° C.

Step a) of the method of the invention is preferably performed at a pressure where water at the temperature applied does not boil yet. For practical purposes the pressure preferably lies in the range from equal to or more than atmospheric pressure (1 bar absolute) to equal to or less than 15 bar (absolute), more preferably a pressure of at most 10 bar (absolute).

Step a) may be carried out in any type of reactor known to the skilled person to be suitable for this purpose. The reactor is preferably a batch reactor, a CSTR reactor or a slurry reactor having an arrangement to move the lignocellulosic biomass mechanically. In a preferred embodiment the reactor contains a lignocellulosic biomass material and in operation a mixture of water and organic acid is sprayed onto the lignocellulosic biomass material.

The lignocellulosic biomass material is preferably contacted with the mixture comprising water and organic acid for a time period in the range of from 0.1 to 10 hours, preferably in the range of from 0.3 to 5 hours, and most preferably 0.4 to 2 hours.

The organic acid and water mixture remaining at the end of step a) is preferably processed for the recycling of the organic acid which is preferably carried out by methods such as pressure swing distillation, extraction or extractive distillation. The recycling of the organic acid is especially preferred where the organic acid is formic acid.

In step a) a first liquid stream comprising hydrolysed hemicellulose and a second stream comprising lignin and cellulose are obtained.

The first liquid stream preferably comprises monomeric sugars, preferably xylose, water and dilute acid. Preferably the first liquid stream comprises an aqueous xylose solution containing equal to or more than 0.5 wt % xylose, more preferably equal to or more than 2 wt % xylose and most preferably equal to or more than 5 wt % xylose. For practical purposes the first liquid stream may preferably contain equal to or less than 50 wt % xylose, more preferably equal to or less than 30 wt % xylose and most preferably equal to or less than 20 wt % xylose, with the remainder preferably containing water.

The second stream preferably comprising cellulose and destructured lignin.

The two streams formed in step a) can be separated using separation techniques known to the skilled person to be suitable for this purpose. Preferably the separation involves removal of liquid from a solid stream by pressing the liquid out from a slurry resulting in the formation of two separate streams; a solid stream and a liquid stream. The separation of the first liquid stream comprising hydrolysed hemicellulose and the second stream comprising lignin and cellulose can for example be carried out by a screw press. In a preferred embodiment the contacting in step a) and the separation are carried out simultaneously.

The lignin and the cellulose present in the lignocellulosic biomass material after separation of the hydrolysed hemicellulose may preferably be subjected to further processing to obtain lignin and cellulose in purer forms which can be used for the production of chemicals and fuels.

In another embodiment at least part of the obtained first liquid stream comprising hydrolysed hemicellulose is recycled and contacted with fresh lignocellulosic biomass material in step a). This advantageously allows for higher concentrations of hydrolysed hemicellulose (in specific of xylose) to be built up in the liquid stream.

In step (b) of the method according to the invention the first liquid stream comprising hydrolysed hemicellulose is maintained at a temperature of at least 130° C. to obtain a second liquid stream comprising furfural.

Furfural as referred to in the present invention is an organic compound which is chemically an aromatic aldehyde with a chemical formula of $C_5H_4O_2$. In pure state, the furfural is a colourless oily liquid but upon exposure to air it quickly becomes yellow. The furfural has various applications. Furfural can be used as a solvent in petrochemical refining to extract dienes which can be used to make synthetic rubber from other hydrocarbons. Furfural, as well as its derivative furfuryl alcohol, can be used either by themselves or together with phenol, acetone, or urea to make solid resins. Such resins can be used in making fibreglass, aircraft components, and automotive brakes. Furthermore furfural can be used as a chemical intermediate in the production of the solvents furan and tetrahydrofuran.

Step b) may be carried out in any type of reactor known to the skilled person to be suitable for this purpose. The reactor can be an autoclave, but is preferably a plug flow reactor, a batch reactor or a CSTR reactor (a continuously stirred tank reactor). In a preferred embodiment step a) and step b) are carried out subsequently in one reactor. Such an embodiment advantageously saves on capital costs. In another preferred embodiment, step b) is carried out in a reactor aligned subsequent to a reactor wherein step a) is carried out.

Step b) is preferably carried out in the presence of a catalyst, preferably an acid catalyst. More preferably, step b) is carried out in the presence of an inorganic acid catalyst. The acid catalyst preferably comprises hydrochloric acid, sulphuric acid, nitric acid and/or phosphoric acid. The acid catalyst used in the present invention is most preferably sulphuric acid as it is easily available and cost effective to use.

In an especially preferred embodiment the first liquid stream obtained from step a) is introduced in step b) in the reactor along with a catalyst, which is preferably an acid catalyst.

In one embodiment the acid catalyst is an inorganic acid that is already added in step a) via a mixture comprising water, an organic acid and an inorganic acid.

In another embodiment the acid catalyst is an inorganic acid that is added in step b), and at least part of the second liquid stream obtained as a product in step b) (such second liquid stream including such inorganic acid) is recycled to step a).

In still another embodiment the acid catalyst is an inorganic acid that is added in step b), separated from the second liquid stream obtained as a product in step b) and recycled to step a).

As indicated above, advantageously the method according to the invention makes it possible to carry out the complete process whilst using the same catalyst(s) in all steps.

The temperature in step b) is preferably in the range of from 130° C. to 300° C., more preferably in the range of from 130° C. to 250° C. As indicated above, the method according to the invention advantageously allows one to further heat a first liquid stream comprising hydrolysed hemicellulose having a temperature of at least 100° C. (as obtained from step a)) to a temperature of at least 130° C. (in step b)) essentially without any intermittent cooling.

Preferably step b) is carried out for an average time of between 0.5 minutes and 120 minutes to obtain the second liquid stream. More preferably step b) is carried out for a time period of equal to or more than 30 minutes or possibly 60 minutes to produce the furfural.

The second liquid stream comprising furfural preferably contains equal to or more than 1 wt % furfural, more preferably equal to or more than 3 wt % furfural and most preferably equal to or more than 5 wt % furfural, and preferably equal to or less than 20 wt % furfural, more preferably equal to or less than 15 wt % furfural, most preferably equal to or less than 10 wt % furfural. The maximum molar yield of the furfural is preferably not less than 50%, more preferably not less than 60%, still more preferably not less than 70%, based on moles C5 sugars in the first liquid stream comprising hydrolysed hemicellulose.

In step c) of the method of the invention the furfural obtained in step b) is separated from the second liquid stream. The separation step is preferably carried out by processes such as solvent extraction, gas stripping, e.g. bubbling air through the mixture, and/or steam stripping. More preferably step c) is carried out by at least one of distillation, extraction and/or extractive distillation.

Without wishing to be bound by any kind of theory, it is believed that the steam stripping process can preferably be based on the spontaneous vaporization of the furfural due to changes in temperature and pressure conditions that are induced in the reactor. More preferably, the furfural is removed by distillation, extraction with a suitable solvent, and/or extractive distillation. Suitable solvents for extraction include for example hydrocarbon solvents such as aromatic or paraffinic solvents, and phosphine oxide solvents such as tetraoctyl phosphine oxide, and mixtures thereof.

Without wishing to be bound by any kind of theory, it is believed that the alteration of the physical-chemical conditions results in desorption of the furfural and vaporization of the remaining components of the product stream. Afterwards the furfural is separated preferably by a cyclone unit and is collected.

Preferably further a spent aqueous solution remains in step c) after the furfural is separated from the second liquid stream. This spent aqueous solution preferably comprises a part of water, the organic acid and optionally any unused acid catalyst.

In a preferred embodiment, the second stream comprising lignin and cellulose obtained in step a) can be subjected to a, preferably first, washing step with water to remove the remnants of hemicellulose. The remnants are further preferably mixed with the first liquid stream comprising hydrolysed hemicellulose to be subjected to step b).

In another preferred embodiment, the second stream comprising lignin and cellulose is subjected to a washing step with water and an alcohol, such as ethanol. Preferably this washing step is carried out as a second washing step subsequent to the above first washing step, but the second washing step may also be carried out in the absence of the first washing step. The purpose of the second washing step is to separate the lignin and the cellulose. During the second washing step the second stream is preferably washed with alcohol and water at a temperature in the range of from 40 to 100° C. and a pressure below 4 bar (absolute), preferably a pressure in the range of from 2 to 4 bar (absolute). Without wishing to be bound by any kind of theory it is believed that the mildly elevated temperature aids in the dissolution of the lignin in the alcohol-water mixture. The temperature is preferably optimized at preferably 50° C. as a higher temperature can lead to the evaporation of the alcohol and lower temperature can be less effective in aiding dissolution of lignin. The residence time of the second stream in the second washing step is preferably 60 minutes. The alcohol used in the second washing step preferably has less than about 4 carbon atoms so that it can be water-miscible. Preferably, an alcohol with carbon chain length of C1 to C3 is used, more preferably ethanol is used. The ratio of ethanol to water used in the second washing step preferably varies in the range of from 1:10 to 10:1. At the end of the second washing step, a third liquid stream comprising lignin is obtained. The lignin can be partially dissolved in the alcohol and water mixture.

After the above second washing step, cellulose is preferably the only component left as a solid, preferably in the form of an undissolved cake. This second solid stream containing cellulose, that is obtained in the second washing step, is preferably essentially free of re-precipitated lignin because the lignin and other dissolved materials preferably remain in solution at all temperatures of the second washing step. Hence, preferably a second solid stream comprising undissolved cellulose and a third liquid stream comprising lignin constitute the product streams of the second washing step.

Preferably the lignin and the cellulose which are obtained from a second washing step may further be subjected to a filtration step, preferably using a filter press. Such a filtration step is preferably vacuum aided to speed up the process. The second solid stream comprising cellulose can be retained on the filter mesh and the third liquid stream comprising lignin can be collected as a filtrate in the vessel. This cellulose may preferably be dried before it is subjected to further processing.

The third liquid stream containing lignin obtained as the filtrate after the separation of cellulose may then be further preferably processed for the recovery of lignin. The cellulose and the lignin thus obtained may preferably undergo further processing before they are provided for commercial use.

Generally, a cellulose-rich solid product obtained by the aforementioned process may be used in industrial cellulose applications directly, with or without drying, or subjected to further processing to either modify the cellulose or convert it into glucose. The cellulose-rich solid product preferably may be processed into paper products by any convenient methods, as those disclosed in Macdonald, Papermaking and Paperboard Making, Vol. 3, TS 1048.J66, 1969. The cellulose-rich solid product may also useful as fluff pulp, which is commonly used in absorbent applications such as diapers and consumer wipes. Cellulose recovered from the solid phase is particularly suitable for manufacturing dissolving pulp (also known as .quadrature.-cellulose), when its purity is 85% by weight or more. In some cases, cellulose of that purity is obtained simply by washing and drying the separated solid phase. If needed, the recovered cellulose can be further purified using various techniques, such as bleaching. Cellulose having a purity of 95 wt % or more can be obtained in this manner. The cellulose obtained in the process of the invention in most cases is easily and rapidly hydrolyzed to glucose and soluble glucose oligomers. The presence of lignin on the surface of the cellulose fibres is believed to hinder the enzymatic hydrolysis of cellulose for the formation of sugars. The lignin is believed to form a physical barrier to water, thus causing the hydrolysis to proceed slowly. In the method according to the invention as described above, the efficient removal of lignin exposes more cellulose at the surface of the fibres, allowing better contact with water (and added enzymes or other catalyst), and therefore increasing the rate of reaction. The cellulose can be catalytically or thermally converted to various organic acids, alcohols and other materials.

Lignin produced in accordance with the invention has high purity. It is essentially free from sulphur and other chemicals and can preferably be used as a fuel. As a solid fuel, lignin is similar in energy content to coal. Lignin can act as an oxygenated component in liquid fuels, to enhance octane while meeting standards as a renewable fuel. The lignin produced herein can preferably also be used as a chemical precursor for producing lignin derivatives. The lignin can preferably be mixed with formaldehyde up to 20% and hence can be used in the preparation of polyphenolic polymers such as Bakelite.

The method according to the present invention is hereinbelow exemplified in conjunction with the non-limiting process flow diagram shown in FIG. 1.

As shown, the process of FIG. 1 includes a step a), herein also referred to as cooking step (102), wherein the lignocellulosic biomass material is cooked at an elevated temperature in the presence of a mixture comprising water and an organic acid. Preferences for this step are as described above for step a). In this step (102), a part of the hemicellulose is illustrated to be hydrolysed to monomer sugars. In FIG. 1. the sugars formed are mainly C5 sugars such as xylose. Further, the lignin which is present in the lignocellulosic biomass material is destructured without being removed.

The cooking step (102) results in the formation of two streams: a first stream comprising hydrolysed hemicellulose (monomeric sugars), preferably xylose, water and dilute acid; and a second stream comprising cellulose and destructured lignin. The organic acid and water mixture remaining at the end of cooking step (102) is preferably processed for the recycling of the organic acid (not explicitly illustrated in FIG. 1). The retrieval of the organic acid and water mixture is preferably carried out as described hereinbefore for step a) by methods such as pressure swing distillation, extraction or extractive distillation.

The two streams formed as a result of the cooking step can be separated using separation techniques as described hereinbefore for step a), such as for example a screw press. As illustrated in FIG. 1. the cooking step (102) and the separation step are preferably carried out simultaneously.

The first stream obtained in step (102) as previously mentioned is rich in sugars. In FIG. 1. the obtained first stream is subsequently subjected to another step of heat treatment (104) (illustrative for step b)) for the production of a product stream comprising the furfural. Preferences for this step are as described above for step b). In the preferred embodiment of FIG. 1, the first liquid stream is introduced in the reactor along with a catalyst, which is preferably an acid catalyst, most preferably sulphuric acid. The product stream obtained as a result of step (104) primarily comprises the furfural. The maximum molar yield of the furfural is preferably not less than 50%, more preferably not less than 60%, still more preferably not less than 70%.

The heat treatment step (104) in FIG. 1 is preferably followed by a separation step (106) (illustrative for step c)) in order to obtain furfural from the product stream of the heat treatment step (104). Preferences for separation step (106) are as described hereinabove for step c).

The furfural obtained can be derivatised to form furfuryl alcohol or other industrially applicable derivatives of the furfural which are also in the scope of the invention (not illustrated in FIG. 1.).

As illustrated in the preferred embodiment of FIG. 1, a spent aqueous solution remains after the furfural is separated from the product stream. This spent aqueous solution preferably comprises a part of water, the organic acid (formic acid) and unused acid catalyst.

In the preferred embodiment of FIG. 1, the second stream formed at the end of the separation step, for example in the screw press, is subjected to a washing step with water (108) to remove the remnants of hemicellulose. The remnants are further preferably mixed with the first stream and are thereby subjected to the heat treatment step (104) to form the furfural.

The second stream comprising lignin and cellulose is further preferably subjected to a second washing step (not illustrated in FIG. 1) in the presence of water and ethanol. Preferences for this second washing step are as described above.

The process according to the invention is further illustrated by means of the following non-limiting simulated examples.

EXAMPLE 1

Hydrolysis of Birch Wood Chips

Birch wood sawdust were contacted with an 1 wt % aqueous solution of formic acid in a weight ratio of birch wood to aqeuous solution of 1 to 9.57 at about 155° C. and 5 bar in an 300 cc autoclave during 240 minutes in order to hydrolyse lignocellulose in the birch wood chips.

The results are illustrated in table 1 below. As illustrated by the total recovered xylose yield in table 1, xylose was obtained in yields up to about 7 wt %. The mixture of xylose and furfural obtained may be less suitable for fermentation due to the presence of furfural but is a very good starting point for the further production of furfural.

EXAMPLE 2

Hydrolysis of Bagasse

Bagasse was contacted with an 1 wt % aqueous solution of formic acid in a weight ratio of bagasse to aqeuous solution of 1 to 10 at about 155° C. and 5 bar in an 300 cc autoclave during 3 hours in order to hydrolyse lignocellulose in the bagasse. Hereafter the contents of the autoclave were filtered. The filtrate was recycled for a second round to hydrolyse a second fresh batch of bagasse and the filtrate obtained from the second round was recycled for a third round to hydrolyse a third fresh batch of bagasse. The residues after each filtration were washed with fresh water (in a weight ratio of bagasse to water of 1 to 10). The results are illustrated in tables 2a and 2b below. As illustrated, by recycling the filtrate, xylose yields (not including furfural yield) of more than 3 wt % can readily be obtained. As furthermore illustrated, also acetic acid is removed, making the residual cellulose very suitable for fermentation purposes.

EXAMPLE 3

Furfural Production

A 5 wt % xylose aqueous solution (representative for a stream of hydrolysed hemicellulose) with 1 wt % formic acid or 0.5 wt % sulphuric acid is introduced in a plug flow reactor and an autoclave, respectively, at 220~230° C. and 30 bar. The results are illustrated in the tables 3, 4, 5 and 6 given below:

TABLE 1

Hydrolysis of birch wood sawdust

| Reaction time (min) | Pressure (bar) | Temp (° C.) | Glucose yield ** wt % | Xylose yield ** wt % | HMF yield ** wt % | Furfural yield ** wt % | total recovered xylose *** wt % | Lignin yield ** wt % |
|---|---|---|---|---|---|---|---|---|
| 4 * | 3.70 ± 0.10 | 144.80 ± 1.80 | 0.10 ± 0.00 | 0.50 ± 0.40 | 0.00 ± 0.00 | 0.05 ± 0.05 | 0.58 ± 0.47 | 1.80 ± 0.00 |
| 9 * | 4.20 ± 0.20 | 149.40 ± 0.40 | 0.30 ± 0.00 | 1.25 ± 1.05 | 0.00 ± 0.00 | 0.20 ± 0.20 | 1.59 ± 1.31 | 2.70 ± 0.00 |
| 38 * | 4.55 ± 0.25 | 151.50 ± 0.50 | 0.20 ± 0.00 | 2.30 ± 1.20 | 0.05 ± 0.05 | 0.45 ± 0.35 | 3.05 ± 1.79 | 4.50 ± 0.00 |
| 122 * | 5.20 ± 0.00 | 153.55 ± 0.25 | 0.40 ± 0.00 | 3.35 ± 0.55 | 0.10 ± 0.00 | 1.20 ± 0.20 | 5.22 ± 0.88 | 5.40 ± 0.00 |

TABLE 1-continued

Hydrolysis of birch wood sawdust

| Reaction time (min) | Pressure (bar) | Temp (° C.) | Glucose yield ** wt % | Xylose yield ** wt % | HMF yield ** wt % | Furfural yield ** wt % | total recovered xylose *** wt % | Lignin yield ** wt % |
|---|---|---|---|---|---|---|---|---|
| 166 * | 5.35 ± 0.05 | 154.15 ± 0.45 | 0.70 ± 0.00 | 3.40 ± 0.00 | 0.15 ± 0.05 | 2.20 ± 0.20 | 6.84 ± 0.34 | 7.20 ± 0.00 |
| 241 * | 5.30 ± 0.30 | 154.75 ± 0.05 | 1.00 ± 0.00 | 2.70 ± 0.10 | 0.20 ± 0.00 | 2.70 ± 0.10 | 6.94 ± 0.06 | 7.20 ± 0.00 |

*** The total recovered xylose yield was determined by calculating the theoretical amount of xylose needed for the formation of the measured yield of furfural and adding such theoretical amount of xylose to the measured yield of xylose in column 5.
** Yield percentages are determined in solution and calculated based on the initial weight of birch wood chips.
* Average ± Deviation as determined on samples taken in duplo
HMF = hydroxymethylfurfural TABLE 2a Hydrolysis of bagasse

| Round | Fresh biomass added (g) | Water added (g) | FA added (g) | Filtrate recycled (g) | Total solution (g) | Filtrate or water wash (g) | Dissolved biomass recycled (g) | Total biomass input (g) |
|---|---|---|---|---|---|---|---|---|
| 1 | 19.36 | 199.76 | 2.03 | 0.00 | 201.79 | 134.16 | 0.00 | 19.36 |
| 2 | 19.73 | 69.84 | 0.70 | 130.21 | 200.75 | 130.43 | 4.08 | 23.81 |
| 3* | 18.85 | 74.67 | 2.01 | 126.29 | 202.97 | 153.30 | 6.34 | 25.19 |

TABLE 2b

Hydrolysis of bagasse

| Round | Sample | Xylose wt %[1] | Xylose wt % in total[1] | Furfural wt %[1] | Furfural wt % in total[1] | HMF wt %[1] | HMF wt % in total[1] | Acetic acid wt %[1] | Acetic acid wt % in total[1] | Products wt %[1] | Product wt % in total[1] |
|---|---|---|---|---|---|---|---|---|---|---|---|
| 1 | Filtrate | 1.74 | 1.95 | 2.76 | 3.45 | 0.21 | 0.25 | 4.06 | 4.77 | 8.77 | 10.41 |
|   | Water wash | 0.21 |  | 0.68 |  | 0.04 |  | 0.71 |  | 1.64 |  |
| 2 | Filtrate | 1.94 | 2.99 | 3.81 | 4.97 | 0.32 | 0.44 | 4.36 | 5.76 | 10.42 | 14.15 |
|   | Water wash | 1.06 |  | 1.16 |  | 0.11 |  | 1.40 |  | 3.73 |  |
| 3 | Filtrate | 2.35 | 3.04 | 4.93 | 6.36 | 0.47 | 0.59 | 4.30 | 5.28 | 12.05 | 15.27 |
|   | Water wash | 0.70 |  | 1.43 |  | 0.12 |  | 0.98 |  | 3.23 |  |

[1]calculated based on fresh biomass intake

TABLE 3

Furfural production in plug flow reactor with 1 wt % formic acid

| Reaction time (min) | Furfural molar yield (mol %) | Xylose left (mol %) | Conversion (mol %) | Selectivity (mol %) |
|---|---|---|---|---|
| 0 | 0.00 | 100.00 | 0.00 | 0.00 |
| 1.22 | 4.79 | 87.03 | 12.97 | 36.95 |
| 1.52 | 8.02 | 82.98 | 17.02 | 47.09 |
| 2.03 | 12.29 | 75.99 | 24.01 | 51.17 |
| 2.43 | 16.46 | 73.88 | 26.12 | 63.01 |
| 3.04 | 20.77 | 67.07 | 32.93 | 63.09 |
| 4.05 | 27.73 | 57.70 | 42.30 | 65.55 |
| 6.08 | 37.23 | 46.77 | 53.23 | 69.93 |
| 9.73 | 41.57 | 41.16 | 58.84 | 70.65 |
| 16.21 | 55.02 | 16.36 | 83.64 | 65.78 |

Conditions of experiment: Water, 230° C., 30 bar, 1 wt % formic acid, 5 wt % xylose, plug flow reactor

TABLE 4

Furfural production in plug flow reactor with 0.5 wt % sulphuric acid

| Reaction time (min) | Furfural molar yield (mol %) | Xylose left (mol %) | Conversion (mol %) | Selectivity (mol %) |
|---|---|---|---|---|
| 0 | 0.00% | 100.00% | 0.00% | 0.00% |
| 1.16 | 46.21% | 26.15% | 73.85% | 62.57% |
| 1.94 | 56.49% | 11.09% | 88.91% | 63.54% |
| 2.33 | 63.01% | 6.38% | 93.62% | 67.31% |
| 2.91 | 63.17% | 5.22% | 94.78% | 66.65% |
| 3.88 | 64.08% | 1.24% | 98.76% | 64.88% |
| 5.82 | 67.61% | 1.22% | 98.78% | 68.44% |
| 9.32 | 56.37% | 0.37% | 99.63% | 56.58% |

Conditions of experiment: Water, 230° C., 30 bar, 0.5 wt % H2SO4, 5 wt % xylose, plug flow reactor.

TABLE 5

Furfural production in autoclave with 1 wt % formic acid

| Reaction time (min) | Furfural molar yield (mol %) | Xylose left (mol %) | Conversion (mol %) | Selectivity (mol %) |
|---|---|---|---|---|
| 0 | 0.00 | 100.00 | 0.00 | 0.00 |
| 2 | 47.40 | 4.65 | 95.35 | 49.71 |
| 5 | 47.25 | 0.00 | 100.00 | 47.25 |
| 10 | 44.18 | 0.00 | 100.00 | 44.18 |
| 15 | 40.15 | 0.00 | 100.00 | 40.15 |
| 30 | 32.89 | 0.00 | 100.00 | 32.89 |
| 78 | 19.09 | 0.00 | 100.00 | 19.09 |
| 120 | 11.36 | 0.00 | 100.00 | 11.36 |

Conditions of experiment: Water, 230° C., 30 bar, 1 wt % formic acid, 5 wt % xylose, autoclave

TABLE 6

Furfural production in autoclave with 0.5 wt % sulphuric acid

| Reaction time (min) | Furfural molar yield (mol %) | Xylose left (mol %) | Conversion (mol %) | Selectivity (mol %) |
|---|---|---|---|---|
| 0 | 0.00 | 100.00 | 0.00 | 0.00 |
| 1.66 | 26.92 | 22.89 | 77.11 | 34.91 |
| 3.5 | 42.17 | 9.98 | 90.02 | 46.84 |
| 4.75 | 42.31 | 3.66 | 96.34 | 43.92 |
| 6.25 | 42.47 | 1.19 | 98.81 | 42.98 |
| 8.5 | 38.52 | 0.29 | 99.71 | 38.64 |
| 16 | 35.98 | 0.00 | 100.00 | 35.98 |
| 30 | 35.68 | 0.00 | 100.00 | 35.68 |
| 60 | 26.42 | 0.00 | 100.00 | 26.42 |
| 121 | 16.18 | 0.00 | 100.00 | 16.18 |

Conditions of the experiment: Water, 220° C., 25.5 bar, 0.5 wt % H2SO4, 5 wt % xylose, autoclave.

We claim:

1. A method for producing furfural from lignocellulosic biomass material, comprising the steps of:
    a) contacting the lignocellulosic biomass material with a mixture comprising water and an organic acid at a temperature of at least 100° C. and a pressure of at most 10 bar (absolute) to obtain a first liquid stream comprising hydrolysed hemicellulose and a second stream comprising lignin and cellulose;
    b) maintaining the first liquid stream comprising hydrolysed hemicellulose at a temperature of at least 130° C. to obtain a second liquid stream comprising furfural; and
    c) separating the furfural obtained in step b) from the second liquid stream, wherein part of the obtained first liquid stream comprising hydrolysed hemicellulose is recycled and contacted with lignocellulosic biomass material in step a).

2. The process of claim 1 further comprising contacting the second stream obtained in step (a) with water thereby removing remnants of hydrolysed hemicelluloses in said second stream.

3. The process of claim 1 wherein the organic acid is selected from the group consisting of formic acid, acetic acid, citric acid, oxalic acid and mixtures thereof.

4. The process of claim 1 wherein the mixture comprising water and the organic acid further comprises an inorganic acid.

5. The process of claim 4 wherein the inorganic acid is selected from the group consisting of hydrochloric acid sulphuric acid, nitric acid, phosphoric acid and mixtures thereof.

6. The process of claim 1 wherein the amount of organic acid present is in the range from 0.1 to 20% by weight.

7. The process of claim 1 wherein step b) is carried out in a batch reactor, a plug flow reactor or a continuously stirred tank reactor.

8. The process of claim 1 wherein step b) is carried out in the presence of an additional inorganic acid catalyst.

9. The process of claim 8, wherein the inorganic acid catalyst is selected from the group consisting of hydrochloric acid, sulphuric acid, nitric acid, phosphoric acid, and mixtures thereof.

10. The process of claim 8 further comprising adding the inorganic acid catalyst in step b), and recycling at least part of the second liquid stream obtained as a product in step (b) to step a).

11. The process of claim 1 wherein step b) is carried out for an average time of between 0.5 minutes and 120 minutes to obtain the second liquid stream.

12. The process of claim 1 wherein step c) is carried out by at least one of distillation, extraction and/or extractive distillation.

* * * * *